US010613021B2

(12) United States Patent
Alic et al.

(10) Patent No.: US 10,613,021 B2
(45) Date of Patent: Apr. 7, 2020

(54) SENSOR DEVICE AND SYSTEM COMPRISING A SENSOR DEVICE

(71) Applicant: B. BRAUN AVITUM AG, Melsungen (DE)

(72) Inventors: Miran Alic, Melsungen (DE); Christof Strohhöfer, Kassel (DE); Waldemar Janik, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 328 days.

(21) Appl. No.: 15/356,186

(22) Filed: Nov. 18, 2016

(65) Prior Publication Data
US 2017/0146446 A1 May 25, 2017

(30) Foreign Application Priority Data

Nov. 23, 2015 (DE) .................. 10 2015 120 215

(51) Int. Cl.
*G01N 21/85* (2006.01)
*G01N 21/03* (2006.01)
(Continued)

(52) U.S. Cl.
CPC ........... *G01N 21/03* (2013.01); *A61M 1/1609* (2014.02); *A61M 1/3406* (2014.02); *G01N 21/85* (2013.01);
(Continued)

(58) Field of Classification Search
CPC ................................ G01N 21/03; G01N 21/85
See application file for complete search history.

(56) References Cited

U.S. PATENT DOCUMENTS 3,697,185 A 10/1972 Kassel et al.
3,802,562 A 4/1974 Kozlov et al.
(Continued)

FOREIGN PATENT DOCUMENTS

DE 15 66 662 8/1970
DE 198 21 903 1/1999
(Continued)

OTHER PUBLICATIONS

European Communication for European Application No. 16 197 475.3, dated Feb. 19, 2018, including English translation, 9 pages.
(Continued)

*Primary Examiner* — Alexander A Mercado
(74) *Attorney, Agent, or Firm* — RatnerPrestia

(57) ABSTRACT

A device for measuring at least one measurand is disclosed which comprises a sensor device with at least one sensor and, via at least one medium-carrying detection path, can be connected to at least one of a plurality of devices outputting at least one flow of a medium to be captured. The at least one sensor is arranged to selectively detect at least one measurand with respect to at least one medium flow output by one of said plurality of devices. A system which includes the sensor device in a centralized way further comprises at least one device outputting the flow of the medium to be measured at least one outlet, wherein one of the devices can be selectively selected and can be connected to the sensor device for a predetermined period of time if several devices outputting a medium flow are connected to the sensor device for measuring at least one measurand.

13 Claims, 2 Drawing Sheets

(51) Int. Cl.
A61M 1/16 (2006.01)
A61M 1/34 (2006.01)
(52) U.S. Cl.
CPC . *A61M 2205/3306* (2013.01); *A61M 2205/84* (2013.01)

(56) References Cited

U.S. PATENT DOCUMENTS

| | | |
|---|---|---|
| 4,211,597 A | 7/1980 | Lipps et al. |
| 4,596,549 A * | 6/1986 | Minami ................ A61M 1/16 210/140 |
| 6,080,583 A | 6/2000 | von Bahr |
| 6,156,002 A | 12/2000 | Polaschegg et al. |
| 2006/0200064 A1 | 9/2006 | Gross et al. |
| 2010/0200506 A1 | 8/2010 | Ware et al. |
| 2012/0198921 A1* | 8/2012 | Lundgreen ........ B01L 3/502715 73/61.41 |

FOREIGN PATENT DOCUMENTS

| | | |
|---|---|---|
| DE | 102 60 046 | 7/2004 |
| WO | WO 2004/057323 | 7/2004 |

OTHER PUBLICATIONS

European Search Report with translation for DE 10 2015 120 215.8 dated Mar. 31, 2017.
German Search Report with translation for DE 10 2015 120 215.8 dated Jul. 5, 2016.

\* cited by examiner

SENSOR DEVICE AND SYSTEM COMPRISING A SENSOR DEVICE

CROSS REFERENCE TO RELATED APPLICATIONS

This application claims priority to German Application DE 10 2015 120 215.8 filed Nov. 23, 2015, the contents of such application being incorporated by reference herein.

FIELD OF THE INVENTION

The invention relates to a sensor device and a system comprising the sensor device and relates in particular to a central device for external single or multiple sensor applications for measuring at least one measurand, as well as to a system which supplies a medium to be measured and comprises said device.

BACKGROUND OF THE INVENTION

In the field of dialysis, for example, sensors are mainly used for monitoring the most varied measuring parameters, and for instance the cleaning level of the blood is determined with the aid of absorbance measurements in the used dialysis liquid (DF), which is a chemical image of the cleaned blood. The absorbance measurements are performed here by means of and/or using an optical UV transmission sensor. In known assemblies, the sensor is a fixed component of the dialysis machine, so that each dialysis machine at which a desired variable or a corresponding measured value is to be output has to be equipped with one or several of such sensor(s), which requires intensive developments and is cost-intensive.

A dialysis center can use several of such dialysis machines at the same time or in a timely staggered manner. In doing so, the rejection of used dialysis liquid is discharged over a common line. Nevertheless, the corresponding sensors have to be plurally provided in the several dialysis machines.

SUMMARY OF THE INVENTION

Thus, the invention relates to the object to provide a device and a system which are able to perform measurements in a used dialysis liquid without disposing a plurality of corresponding and/or similar sensors in several dialysis machines.

This object is achieved according to aspects of the invention by a device for measuring at least one measurand comprising the features of the first independent claim and by a system comprising a centralized device for an external single or multiple sensor device comprising the features of the second independent claim.

The invention relates to the general idea to remove the sensors, carrying out measurements in used dialysis liquids, from the dialysis machine such that a centralized sensor device can be used for several dialysis machines at the same time or in a timely adapted fashion. To this end, the use of the sensor system is reorganized according to aspects of the invention such that the used dialysis liquid is directed through an external device which only comprises one exemplar of each sensor. This drastically reduces the number of sensors employed. In order to be able to operate several dialysis machines, the device may additionally comprise a module which—by a suitable bypassing or switching of flow paths of flows, i.e. flows of media output by a dialysis machine (predominantly fluids or liquids such as the used dialysis liquid of a desired dialysis machine, but without any limitation thereto)—is able to re-route the flows of media through the sensor(s) in the external device. This is possible in particular because known sensors in a dialysis machine detect their values anyway every 3 to 5 minutes. In the meantime, values for other machines can be recorded without having to accept a reduction in resolution, for example.

Instead of focusing on a production of numerous sensors for installation in a dialysis machine, an external centralized sensor device advantageously allows to reduce the number of sensors required for the overall system and to cut costs. Moreover, it will be possible to use further sensors for the measurement of quantitative variables such as creatinine and urea, for example.

In addition, some sensors need an additional device for adding corresponding reagents. With known assemblies, such additional devices require space in a dialysis machine and also have to meet high regulatory requirements. According to aspects of the invention, however, it is possible that all the sensors located in the dialysis liquid drain section can be accommodated in the centralized device. In this case, they are subject to considerably lower regulatory requirements because they represent an in-vitro diagnostic agent. In this respect, the device according to aspects of the invention provides room for elements and components which actually have to be individually present in a dialysis machine. Further advantages result from the fact that even low-cost machines and/or machines from other manufacturers, which usually are not equipped with a separate and/or compatible sensor system in the drain section of the dialysis machine can also be connected to the device and operated in the system network. Further, measured values can be forwarded or transferred to a dialysis machine and/or corresponding databases by the already existing infrastructure such as data management systems, for example.

Specifically, the above-mentioned advantages are achieved and the object is met by a device for measuring at least one measurand, comprising: a sensor device which has at least one sensor and, via at least one medium-carrying detection path, can be connected to at least one of a plurality of devices outputting at least one flow of a medium to be captured, the at least one sensor being arranged to selectively detect at least one measurand with respect to at least one medium flow output by one of the plurality of devices.

A device for measuring at least one measurand is suggested, comprising: a sensor device such as a stand-alone sensor which comprises at least one sensor and, via at least one medium-carrying detection path, can be connected to one of a plurality of (medical) devices such as dialysis machines, which each output a flow of medium (used dialysis fluids/liquids) to be captured as a medium flow, the at least one sensor being arranged to selectively detect at least one measurand with respect to the medium flow output by said one device; and a fluidic unit (for example a switch valve or a multi-port valve) which is arranged upstream of the sensor device, can be (is) connected to the plurality of devices via a plurality of paths carrying medium flows and is connected to the sensor device so as to (selectively) pass on exactly one medium flow to the sensor device, wherein the fluidic unit is arranged to provide a flow control (performed in a processor/CPU) for the flows of media to be captured, namely by selectively choosing one of the plurality of medium flows output by the plurality of devices via the plurality of paths carrying medium flows and by supplying the one selected medium flow to the at least one sensor of the sensor device.

Preferably, the at least one sensor is arranged to detect the at least one measurand with respect to the medium flow along a fluid path or an air path.

Preferably, the sensor device constitutes a sensor device which is centralized for a plurality of devices and is connected to at least one output and/or outlet of a dialysis machine via a liquid path or an air path.

Preferably, the at least one sensor is arranged to detect a clearance and/or a concentration of an analyte in the medium flow as the at least one measurand.

Preferably, a flow-controlling fluidic unit arranged upstream of the sensor device is connected so as to pass on at least one medium flow to the sensor device, the fluidic unit being arranged to supply, in a specifically selectable manner, the at least one sensor device with at least one of a plurality of medium flows which are output by the plurality of devices outputting the plurality of medium flows and/or the sensor device is arranged, in a specifically selectable manner, to detect at least one of a plurality of measurands of a selected device whose medium flow is fed to the sensor device.

Preferably, the fluidic unit is arranged to supply the sensor device with medium flows from the plurality of devices in a timely controlled manner and in a predetermined switching scheme, and/or to supply the sensor device with a currently selected medium flow from a currently selected device for a predetermined period of time.

Preferably, the predetermined period of time can be adapted or is adapted to detection times of a sensor system in the currently selected device, and a plurality of predetermined periods of time are provided to be adaptable or to be adapted to detection times of a sensor system of each of the plurality of connected or connectable devices and are made available alternately in the manner of a time multiplex.

Preferably, among a plurality of predetermined periods of time at least one predetermined period of time having a fixed or adjustable duration is provided for a sensor-less device.

Preferably, a selection of a device can be enforced by a user and can only be canceled by the latter at any points in time.

Preferably, at least one multi-port valve is provided which is arranged to be connectable at the input side with a plurality of devices outputting medium flows, to be connected to the sensor device at the output side and to supply the sensor device with one medium flow each from the plurality of devices outputting medium flows. Instead of the at least one multi-port valve, it is also possible to provide a clever combination of simple shut-off valves with which the device according to aspects of the invention is implemented.

Preferably, an interface to a data management and/or communication device is provided for a transmission and/or further processing of measured data and/or measurands in an associated device and/or a database.

Preferably, an additional device such as a pump or a syringe or a valve is provided on the sensor device and arranged to add a reagent required by the sensor.

A system is suggested that comprises a centralized device for an external single or multiple sensor device includes a centrally arranged device (comprising at least a sensor device and a fluidic unit) for measuring at least one measurand as described above; and at least one (medical) device (such as a dialysis machine) outputting the flow of the medium to be measured at at least one outlet, wherein one of the devices (dialysis machines) can be selectively selected and can be connected to the (centrally arranged) device for a predetermined period of time if several devices (dialysis machines) outputting a medium flow (dialysis liquid/fluid) are connected to the (centrally arranged) device for measuring at least one measurand.

Preferably, the system comprises a data management and/or communication device arranged to receive captured information, data and/or measured values from the device for measuring at least one measurand.

Preferably, the data management and/or communication device is arranged to transfer information, data and/or measured values received from the device for measuring at least one measurand to a predetermined device outputting a medium flow and/or to store these in a database.

Preferably, the data management and/or communication device is arranged to transfer control and/or closed-loop control instructions, which are output by a device outputting a medium flow, to the device for measuring at least one measurand.

Preferably, the system comprises a display device for displaying information, data and/or measured values captured by the device for measuring at least one measurand and/or for displaying information or instructions, relevant to system-related control and/or closed-loop control functions, output by a device outputting a medium flow.

BRIEF DESCRIPTION OF THE DRAWINGS

The invention is best understood from the following detailed description when read in connection with the accompanying drawings.

DETAILED DESCRIPTION OF THE PREFERRED EMBODIMENTS

Figure 1:
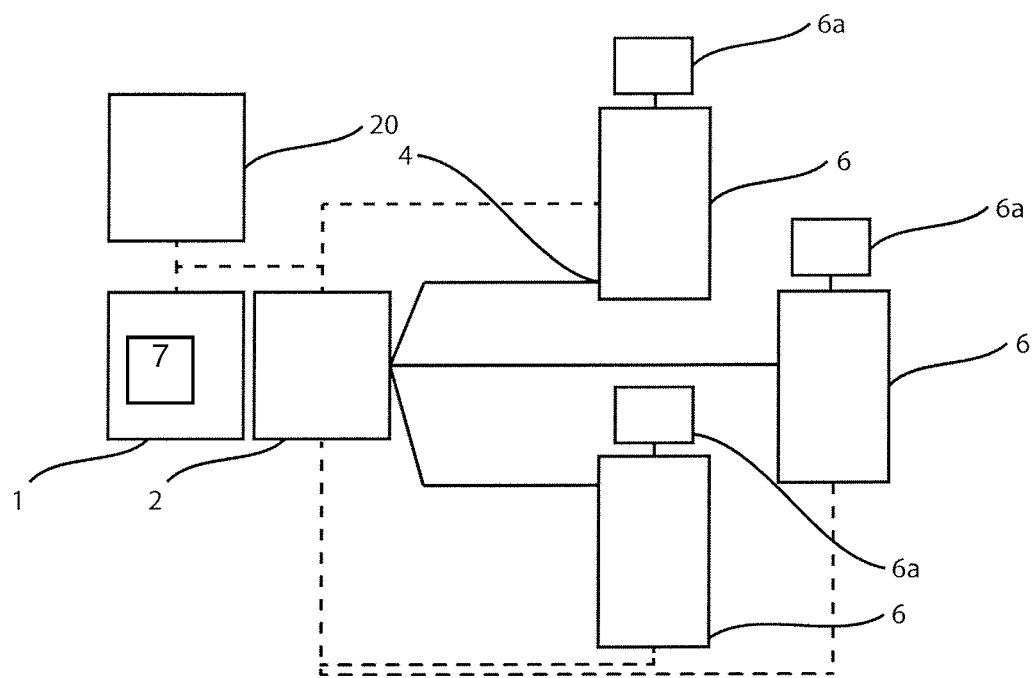
FIG. 1 shows in a schematic illustration a system for a timely adapted measurement of various variables in a used dialysis liquid via systematic connections of the liquid outputs of dialysis machines comprising a centralized sensor device according to an exemplary embodiment.

In the following description of the Figures, identical or functionally identical elements and components in the individual Figures are designated with the same reference numerals and are expediently not redundantly described. In those cases in which a following exemplary embodiment functionally corresponds to at least one preceding embodiment, i.e. if corresponding functions, arrangements and/or modes of operation are similarly contained, only the differences will be discussed for convenience.

According to the following exemplary embodiments, a device and a system comprising said device for measuring various variables (conductivity, temperature, pH value, Kt/V, concentrations of analytes such as creatinine, urea and the like and of electrolytes such as sodium and the like) are connected to the dialysis machine via the liquid output or an air path with the aid of a centralized sensor device. A suitable flow control unit allows to detect various measurands of selected machines. A data management—and/or communication application allows for the transfer or transmission of measured information, data and/or values into the dialysis machine (e.g. for displaying these on a display device or for instance as control and closed-loop control instructions) and/or into a database.

FIG. 1 shows in a schematic illustration a system for the timely adapted measuring of various variables in a used dialysis liquid through systematic connections between the liquid outputs of dialysis machines and a centralized sensor device (stand-alone sensor). An additional connection to a network for data communication between a sensor, a server/processor (CPU), databases and at least one dialysis machine is indicated in broken lines. In this way, any values collected by the sensor device can be forwarded to further processing, for instance to a screen of the dialysis machine for being displayed thereon.

Specifically, FIG. 1 shows three dialysis machines 6 each comprising an input and/or display device 6a, for example a screen, a keyboard and the like, and an outlet 4 for the dialysis liquid. For the sake of clarity of the illustration, only one outlet is designated with the reference numeral 4 in FIG. 1. Moreover, there is no limitation with regard to the number of dialysis machines. Depending on the design, almost any numbers of dialysis machines can be integrated in the system according to the exemplary embodiment. The individual outlets 4 of each of the dialysis machines 6 are separately guided to inlets of a fluidic unit 2 constituting a smart fluid management device. The interior of the fluidic unit 2 comprises at least one multi-port valve to be described later, which is arranged to open and close fluid paths or fluid lines in a controlled manner such that the fluidic unit 2 passes on at least one chosen, i.e. selected fluid or liquid flow forming the flow of a medium output from a dialysis machine, and blocks fluid flows from other dialysis machines which have not been chosen/selected. The passed fluid flow is output at an outlet of the fluidic unit 2 and is supplied to a sensor device 1 for being measured there.

FIG. 1 shows a system comprising three dialysis machines 6, for instance, (with the option that almost any number of dialysis machines can be connected and insofar there is no limitation with respect to the number of dialysis machines), which each have connected their (dialysis) liquid output 4 to the sensor device 1 (the stand-alone sensor). The selection of one of the dialysis machines 6 to be measured may be carried out by a suitable design of a flow control unit, i.e. fluidic unit 2, which is provided upstream of the sensor device 1 and works according to a smart fluid management scheme. It is to be noted that the fluidic unit 2 may be optionally provided, which means that the connection and/or disconnection of fluid flows may also be effected directly on the dialysis machine 6 by suitable valve means and the like, for instance, or that the fluidic unit 2 may be designed so as to be integrated in the sensor device 1.

The sensor device 1 may further comprise one or more different (not illustrated) sensors as well as associated mechanical and electronic systems, such as e.g. (reagent) pumps 7, control units, arithmetic units and the like which are known per se. A communication and/or data management device 20 or a corresponding application allows to send information to the dialysis machine. Such information may consist in a captured concentration value or a clearance (Kt/V) value, for example. However, it is also possible to simultaneously send or transmit control instructions in order to control a blood flow, for instance, making it possible for other methods to determine blood-related concentrations.

The detected values are available to the dialysis machine 6 and can be output for being displayed on the screen 6a and/or written in a (not illustrated) database. In the latter case, the data obtained in this way can be analyzed over a longer period of time.

Figure 2:
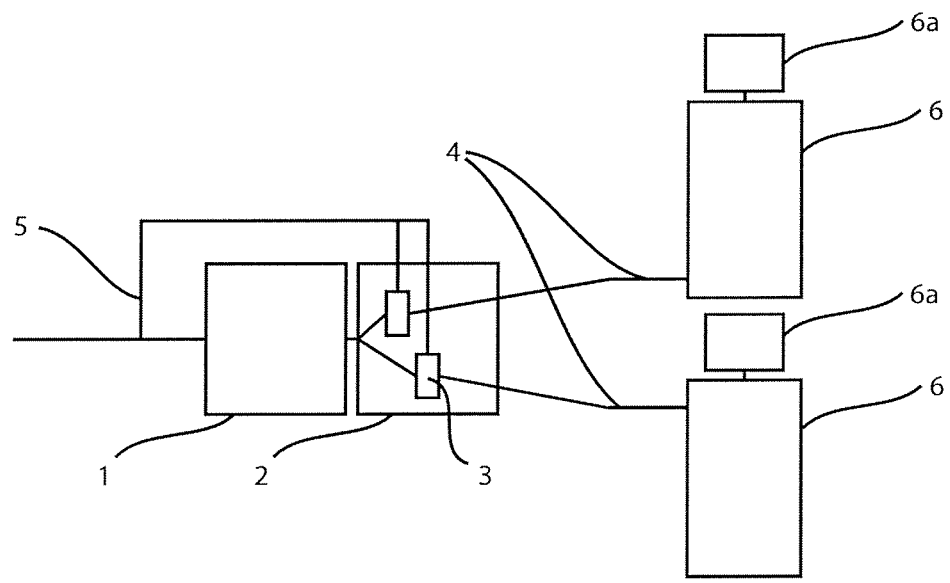
FIG. 2 is a schematic illustration of a fluidic system which is arranged to control and manage flows from different dialysis machines and can be used in the exemplary embodiment according to FIG. 1.

FIG. 2 shows a schematic illustration of a fluidic system which is arranged to control and manage the flows from different dialysis machines 6 and can be used in the exemplary embodiment according to FIG. 1.

Specifically, FIG. 2 illustrates two dialysis machines 6 each having an associated operating and/or display device 6a with one dialysis liquid outlet 4 each. Each of the dialysis liquid flows delivered as a medium flow by the dialysis machines 6 at their dialysis liquid outlets 4 is supplied to a corresponding inlet of the fluidic unit 2. Provided in the fluidic unit 2 is at least one multi-port valve 3 which is arranged to separately conduct or to block each individual dialysis liquid flow in a predetermined and controlled manner and for fixed or adaptable periods of time in each case.

By way of example and according to FIG. 2, it is possible that the dialysis liquid delivered by the upper dialysis machine 6 can be passed on to the sensor device 1, while the dialysis liquid output by the lower dialysis machine 6 can be blocked at the multi-port valve 3 and hence is not conveyed to the sensor device 1. All those dialysis liquid flows which are not passed on to the sensor device 1 may be discharged out of the fluidic unit 2 for instance by rejection lines 5 branching off from the multi-port valve 3, in order to ensure a continual drainage of the dialysis liquid even from dialysis machines 6 which have not been selected.

It is preferred that said periods of time are specified or selected in accordance with a time behavior of detected values at a respective dialysis machine 6 according to a treatment process which is carried out there. In other words, the process of passing on a dialysis liquid of a particular dialysis machine 6 for being measured in the sensor device 1 is carried out preferably in those periods of time or at those points in time where a recording or detection of values is supposed to be done at the particular dialysis machine 6 (for instance every 3 to 5 minutes). The dialysis liquid of another dialysis machine 6 can be measured in other times. To this end, several dialysis machines 6 may be operated such or may perform their treatment such, for instance, that they receive the respectively required values with a suitable time offset.

It goes without saying that the components and/or the parts of the system may also be provided in multiple form. By way of example, if within existing cycle times the number of already connected dialysis machines 6 does not allow to connect further dialysis machines 6, it is possible to add a second fluidic unit 2 and/or a second sensor device 1 for measuring medium flows from further dialysis machines 6.

According to the exemplary embodiment of a flow control unit or fluidic system shown in simplified form in FIG. 2, several dialysis machines 6 can be connected to a solitary sensor device 1. The illustration of digital connections has been omitted from FIG. 2 for reasons of clarity, but it is self-evident that information can be transferred between a corresponding dialysis machine 6 and the solitary sensor device 1.

The core of the previously described smart fluid management scheme in accordance with the fluidic unit 2 is represented by at least one multi-port valve 3 which is illustrated according to the exemplary embodiment in a variant with two ports. The output or outlet 4 for the dialysis liquid of a dialysis machine 6 is connected to the at least one multi-port valve 3 via the fluidic unit 2. This allows to control the flows in the machine. A digital interface (not shown) offers the possibility to determine the machine for which the dialysis liquid is to be examined. The other paths are discharged to the drain. The measured values may then be transmitted to the corresponding machine for illustration and/or further processing.

Figure 3:
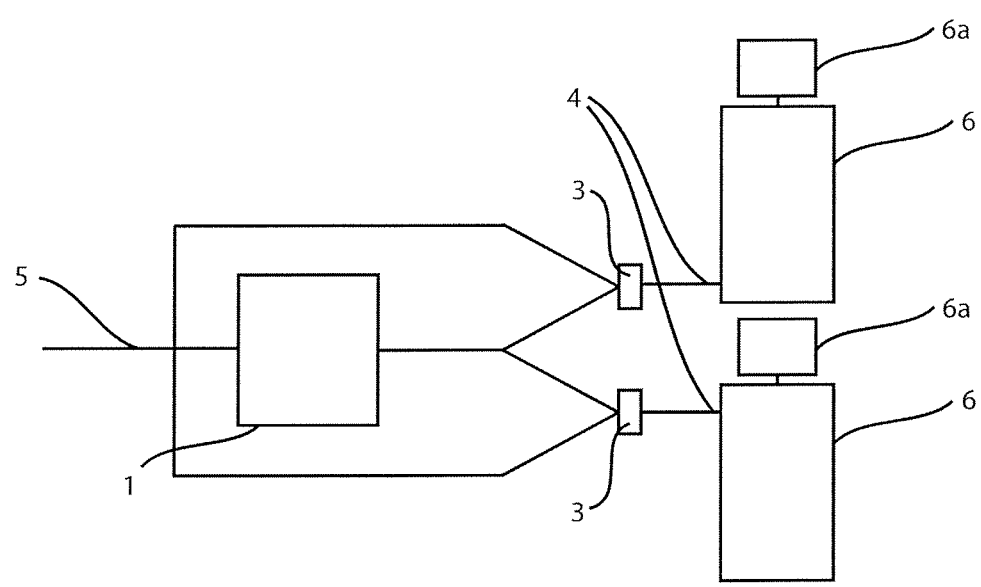
FIG. 3 is a schematic illustration of a modification of the fluidic system according to FIG. 2, which is arranged to control and manage flows from different dialysis machines and can be used in the exemplary embodiment according to FIG. 1.

FIG. 3 shows a schematic illustration of a modification of the fluidic system according to FIG. 2, which is arranged to control and manage flows from different dialysis machines and can be used in the exemplary embodiment according to FIG. 1.

According to FIG. 3, the at least one multi-port valve 3 is arranged directly on the outlet 4 of the dialysis machine 6. It is of further advantage that the arrangement of the lines is more flexible here while maintaining the previously described measuring principle.

According to aspects of the invention, there are cost savings in terms of the installation of many sensors, it is possible to use several sensors for the investigation or detection of a very wide range of variables such as Kt/V, creatinine, urea, but also for enzymatic tests, the regulatory requirements which have to be met are lower by a possible classification as an in vitro diagnostic agent, and even dialysis machines which are not equipped with an own sensor system benefit from the cited advantages of the described sensor system.

Thus, a device for measuring at least one measurand and a system containing the device for external single or multiple sensor devices in a centralized manner have been described above. The device comprises a sensor device which has at least one sensor and, via at least one medium-carrying detection path, can be connected to at least one of a plurality of devices outputting at least one flow of a medium to be captured, the at least one sensor being arranged to selectively detect at least one measurand with respect to at least one medium flow output by one of said plurality of devices. The system further comprises at least one device outputting the flow of the medium to be measured at at least one outlet, wherein one of the devices outputting a medium flow can be selectively selected and can be connected to the device for a predetermined period of time if several devices outputting a medium flow are connected to the device for measuring at least one measurand.

It shall be understood that the invention is not limited to the described exemplary embodiments, in particular not to the dialysis machine and the dialysis liquid which have only been taken as an example and to the numeric values and orders of magnitude which have been given in their context, but obvious modifications and equivalent solutions can be inferred by the person skilled in the art within the scope of protection defined by the following claims.

The invention claimed is:

1. A device for measuring at least one measurand, the device comprising:
a sensor device which comprises at least one sensor and, via at least one medium-carrying detection path, is connected to a plurality of dialysis machines which each output a flow of a medium to be captured as a respective medium flow, the at least one sensor being arranged to selectively detect the at least one measurand with respect to the respective medium flow output by each of the plurality of dialysis machines and output a respective measured value of each detected measurand; and
a fluidic unit arranged upstream of the sensor device, the fluidic unit comprising at least one multi-port valve or a combination of shut-off valves connected at an input side to the plurality of dialysis machines via a plurality of paths carrying the respective medium flows, and connected at an output side to the sensor device, the at least one multi-port valve or combination of shut-off valves being configured to separately conduct or to block each individual one of the plurality of paths in a predetermined and controlled manner so as to pass on exactly one of the respective medium flows to the sensor device, wherein
the fluidic unit is arranged to provide a flow control for the respective medium flows by selectively choosing one of the respective medium flows and by supplying the one selected respective medium flow to the at least one sensor of the sensor device;
wherein the fluidic unit is configured to supply the sensor device with the respective medium flows according to a switching scheme in which each respective medium flow is supplied to the sensor device for a respective predetermined period of time, and each respective predetermined period of time is specified in accordance with a time behavior of the detected measurand at a respective one of the plurality of dialysis machines according to a respective treatment process carried out at the respective one of the plurality of dialysis machines.

2. The device according to claim 1, wherein the at least one sensor is arranged to detect the at least one measurand with respect to the respective medium flow along a fluid path or an air path.

3. The device according to claim 1, wherein the plurality of dialysis machines each comprises a respective dialysis machine and each of the plurality of paths comprises a liquid path or an air path.

4. The device according to claim 1, wherein the at least one sensor is arranged to detect a clearance and/or a concentration of an analyte in the respective medium flow as the at least one measurand.

5. The device according to claim 1, wherein the sensor device is arranged to detect, in an individually selectable manner, a plurality of measurands.

6. The device according to claim 5, wherein the fluidic unit is configured to permit a user to selectively enforce a selection of one of the plurality of dialysis machines, whereupon the selection of the one of the plurality of dialysis machines can only be canceled by the user.

7. The device according to claim 1, wherein among a plurality of predetermined periods of time at least one predetermined period of time has a fixed or adjustable duration that is provided for a sensor-less one of the plurality of dialysis machines.

8. The device according to claim 1, wherein an interface to a data management and/or communication device is provided for a transmission and/or processing of measured values for the at least one measurand in a further associated device and/or a database.

9. The device according to claim 1, wherein an additional device is provided on the sensor device and is arranged to add a reagent required by the sensor.

10. The device according to claim 1, further comprising:
a display device for displaying each respective measured value and/or for displaying information or instructions, related to system-related control and/or closed-loop control functions, output by at least one of the plurality of dialysis machines outputting the respective medium flow.

11. The device according to claim 1, further comprising:
a data management and/or communication device arranged to receive each respective measured value.

12. The device according to claim 11, wherein the data management and/or communication device is arranged to transfer each respective measured value and/or to store each respective measured value in a database.

13. The device according to claim 11, wherein the data management and/or communication device is arranged to transfer control and/or closed-loop control instructions, which are output by at least one of the plurality of dialysis machines outputting the respective medium flow, to the device for measuring at least one measurand.

* * * * *